US008888677B2

(12) United States Patent
Beckman et al.

(10) Patent No.: US 8,888,677 B2
(45) Date of Patent: Nov. 18, 2014

(54) PRESSURE LIMITING DEVICE FOR GASTRIC BAND ADJUSTMENT

(75) Inventors: Andrew T. Beckman, Cincinnati, OH (US); Scott A. Woodruff, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 551 days.

(21) Appl. No.: 12/944,831

(22) Filed: Nov. 12, 2010

(65) Prior Publication Data

US 2012/0123194 A1 May 17, 2012

(51) Int. Cl.

| | |
|---|---|
| ***A61F 2/00*** | (2006.01) |
| ***A61F 13/00*** | (2006.01) |
| ***A61F 5/00*** | (2006.01) |
| ***A61M 25/10*** | (2013.01) |
| ***A61M 5/48*** | (2006.01) |
| *A61M 5/31* | (2006.01) |
| *A61M 5/315* | (2006.01) |

(52) U.S. Cl.

CPC ........ *A61F 5/0056* (2013.01); *A61M 2205/583* (2013.01); *A61M 2005/3125* (2013.01); *A61M 25/1018* (2013.01); *A61F 5/003* (2013.01); *A61M 5/31581* (2013.01); *A61M 5/3148* (2013.01); *A61M 5/486* (2013.01); *A61M 5/488* (2013.01)

USPC .............................................. 600/37; 606/51

(58) Field of Classification Search

USPC .............................................. 600/37; 606/51

See application file for complete search history.

(56) References Cited

U.S. PATENT DOCUMENTS

| | | | |
|---|---|---|---|
| 5,163,952 | A | 11/1992 | Froix |
| 6,067,991 | A | 5/2000 | Forsell |
| 6,461,292 | B1 | 10/2002 | Forsell |
| 6,470,892 | B1 | 10/2002 | Forsell |
| 6,824,561 | B2 | 11/2004 | Soykan et al. |
| 7,416,528 | B2 | 8/2008 | Crawford et al. |
| 7,442,165 | B2 | 10/2008 | Forsell |
| 7,621,863 | B2 | 11/2009 | Forsell |
| 7,699,770 | B2 | 4/2010 | Hassler, Jr. et al. |
| 7,775,215 | B2 | 8/2010 | Hassler, Jr. et al. |
| 7,850,660 | B2 | 12/2010 | Uth et al. |
| 8,252,337 | B2 | 8/2012 | Lee et al. |
| 2006/0142794 | A1 | 6/2006 | Lendlein et al. |
| 2006/0199997 | A1 | 9/2006 | Hassler, Jr. et al. |

(Continued)

FOREIGN PATENT DOCUMENTS

| | | |
|---|---|---|
| WO | WO 2006/020370 | 2/2006 |
| WO | WO 2011/005679 | 1/2011 |
| WO | WO 2011/137242 | 11/2011 |

OTHER PUBLICATIONS

International Search Report dated Mar. 5, 2012 for Application No. PCT/US2011/059956.

(Continued)

*Primary Examiner* — Christine Matthews
*Assistant Examiner* — Sunita Reddy
(74) *Attorney, Agent, or Firm* — Frost Brown Todd LLC

(57) ABSTRACT

A pressure sensing or monitoring device may be used with an implantable band system. In some versions, the device may be used with a syringe. The device may comprise a visual indicator for monitoring pressure. The device may govern operation of the syringe by setting a threshold pressure to limit the amount of pressure applied to an implantable band system by the syringe.

6 Claims, 7 Drawing Sheets

270
272
276
280
264
282
272
274
278
256
258

(56) References Cited

U.S. PATENT DOCUMENTS

2007/0213656 A1* 9/2007 Ferdinand ........................ 604/65
2007/0235083 A1* 10/2007 Dlugos .......................... 137/223
2007/0265598 A1 11/2007 Karasik
2008/0015406 A1 1/2008 Dlugos et al.
2011/0009812 A1* 1/2011 Brown ............................ 604/31
2011/0270131 A1* 11/2011 Snow et al. ................... 600/587

OTHER PUBLICATIONS

International Search Report dated Jun. 19, 2012 for Application No. PCT/US2011/037678.

* cited by examiner

PRESSURE LIMITING DEVICE FOR GASTRIC BAND ADJUSTMENT

BACKGROUND

A variety of systems and devices have been made and used for treating morbid obesity. Some such systems and devices include adjustable gastric band systems, which are operable to restrict the flow of food from the esophagus into the stomach. Some gastric bands include a fluid-filled elastomeric bladder with fixed endpoints that encircles the stomach just inferior to the gastro-esophageal junction. When fluid is added to the bladder, the band expands against the stomach, creating a food intake restriction or stoma in the stomach. To decrease this restriction, fluid is removed from the bladder. Examples of gastric bands are disclosed in U.S. Pat. No. 7,416,528, entitled “Latching Device for Gastric Band,” issued Aug. 26, 2008, the disclosure of which is incorporated by reference herein. Another example of such an adjustable gastric band is disclosed in U.S. Pat. No. 6,067,991, entitled “Mechanical Food Intake Restriction Device,” issued May 30, 2000, the disclosure of which is incorporated by reference herein.

To the extent that an adjustable gastric band system includes an injection port configured to receive the needle of a syringe assembly to add or withdraw fluid to or from the gastric band, those of ordinary skill in the art will appreciate that it may be desirable in some settings to locate both the injection port and, more specifically, the center of the injection port (e.g., when the septum of the injection port is at the center of the injection port). Locating the approximate center of the injection port with some degree of accuracy may facilitate addition or withdrawal of fluid via the injection port to adjust the gastric band system. One example of a system and method for identifying the location of an injection port is disclosed in U.S. Pub. No. 2006/0211914, entitled “System and Method for Determining Implanted Device Positioning and Obtaining Pressure Data” published Sep. 21, 2006, and issued Aug. 17, 2010 as U.S. Pat. No. 7,775,215, the disclosure of which is incorporated by reference herein.

Those of ordinary skill in the art will appreciate that it may be advantageous in certain circumstances to sense pressure, strain, and/or other parameters associated with operation of a gastric band device. In some settings, it may be desirable to obtain data indicative of the pressure of fluid in a gastric band. Various examples of methods and devices for obtaining pressure data and other types of data are disclosed in U.S. Pub. No. 2006/0189888, entitled “Device for Non-Invasive Measurement of Fluid Pressure in an Adjustable Restriction Device,” published Aug. 24, 2006, and issued Apr. 20, 2010 as U.S. Pat. No. 7,699,770, the disclosure of which is incorporated by reference herein. Additional examples of methods and devices for obtaining pressure data and other types of data are disclosed in U.S. Pub. No. 2006/0199997, and issued Sep. 13, 2011 as U.S. Pat. No. 8,016,745, entitled “Monitoring of a Food Intake Restriction Device,” published Sep. 7, 2006, the disclosure of which is incorporated by reference herein.

Yet further examples of methods and devices for obtaining pressure data and other types of data are enclosed in U.S. Pub. No. 2008/0015406, entitled “External Mechanical Pressure Sensor for Gastric Band Pressure Measurements,” published Jan. 17, 2008, and issued Apr. 19, 2011 as U.S. Pat. No. 7,927,270, the disclosure of which is incorporated by reference herein. Such parameter data may be obtained before, during, and/or after adjustment of a gastric band, and may be useful for adjustment, diagnostic, monitoring, or other purposes, and may also be obtained with respect to a mechanically actuated gastric band. In settings where a fluid-filled gastric band is used, pressure data may be used to determine whether the amount of fluid in the gastric band needs to be adjusted; and/or for other purposes.

Those of ordinary skill in the art will appreciate that in some instances, particularly in those involving fluid-filled gastric bands, fluids may need to be removed or added in order to, for example, adjust the size of the gastric band. As fluid is added or removed, the pressure within the gastric band and/or other portions of gastric band system may change. In some cases those changes may be significant relative to the pre-existing pressure and may have undesirable consequences if the changes exceed certain levels. For example, sudden pressure drops or other changes may cause tubing or other portions of the gastric band system to collapse.

While a variety of gastric band systems have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
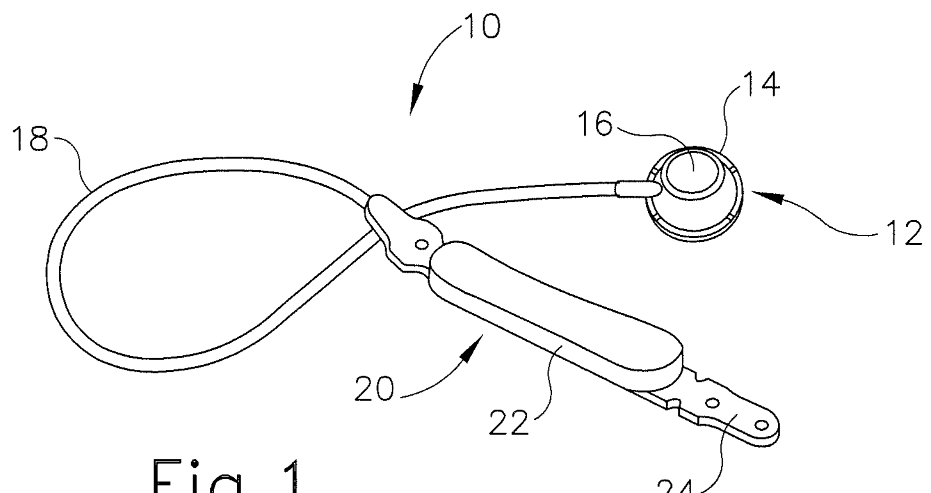
FIG. 1 depicts a perspective view of an implantable portion of an exemplary gastric band system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Gastric Band System

FIGS. 1-4 illustrate an exemplary gastric band system (10). As shown, gastric band system (10) comprises an injection port (12), a gastric band (20), and a catheter (18). Injection port (12) of the present example comprises a port housing (14) and a needle penetrable septum (16). Port housing (14) defines a fluid reservoir (not shown), such that a needle may pierce septum (16) to reach the reservoir and add or withdraw fluid (e.g., saline, etc.) as described in greater detail below. Port housing (14) may be formed of titanium, plastic, or any other suitable material or combination of materials. Septum (16) may be formed of silicone or any other suitable material or combination of materials. Injection port (12) may be subcutaneously secured over a patient's sternum, to the patient's abdominal fascia, or in any other suitable location. In some versions, injection port (12) is configured and operable in accordance with the teachings of U.S. Pub. No. 2005/0283118, entitled "Implantable Medical Device with Simultaneous Attachment Mechanism and Method," published Dec. 22, 2005, and issued Dec. 14, 2010 as U.S. Pat. No. 7,850,660, the disclosure of which is incorporated by reference herein. Alternatively, injection port (12) may have any other suitable configuration and/or operability.

Gastric band (20) of the present example comprises an inflatable bladder (22) that is secured to a flexible strap (24). Inflatable bladder (22) may be formed of silicone or any other suitable material or combination of materials. Catheter (18) provides fluid communication between bladder (22) and the reservoir of injection port (12). Accordingly, a needle that is inserted through septum (16) may be used to add or withdraw fluid from inflatable bladder (22), to adjust the restriction created by gastric band (20) as described in greater detail below. In some versions, gastric band (20) is configured and operable in accordance with the teachings of U.S. Pat. No. 7,416,528, entitled "Latching Device for Gastric Band," issued Aug. 26, 2008, the disclosure of which is incorporated by reference herein. Alternatively, gastric band (20) may have any other suitable configuration and/or operability.

Figure 2:
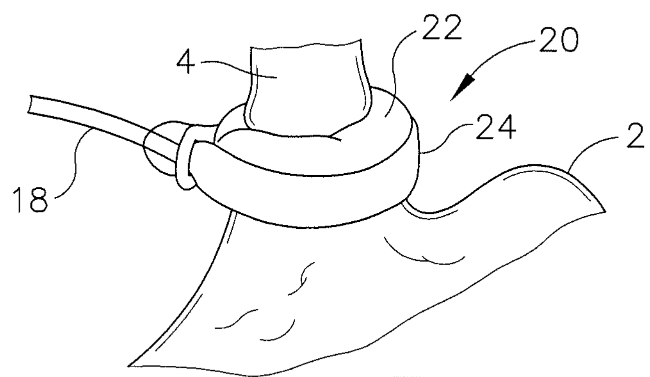
FIG. 2 depicts a perspective view of the gastric band of FIG. 1, showing the band positioned around the gastro-esophageal junction of a patient.

In some settings, gastric band (20) is applied about the gastro-esophageal junction of a patient. In particular, and as shown in FIG. 2, gastric band (20) is installed such that bladder (22) is adjacent to the tissue of the gastro-esophageal junction, with strap (24) on the outside of bladder (22). The ends of strap (24) are secured relative to each other when gastric band (20) is sufficiently wrapped about the patient's stomach (2). While strap (24) is flexible in this example, strap (24) substantially resists stretching along its length. Accordingly, when fluid is added to bladder (22) (e.g., using a needle inserted through septum (16) of injection port (12), etc.), bladder (22) expands and exerts inward forces on the gastro-esophageal junction of the patient. This reduces the size of the internal stoma at the gastro-esophageal junction, thereby creating a restriction on food intake into the patient's stomach (2). It should be understood that the size of this stoma may be decreased by adding more fluid to bladder (22) to create a greater degree of restriction; or increased by withdrawing fluid from bladder (22) to reduce the degree of restriction.

Figure 3:
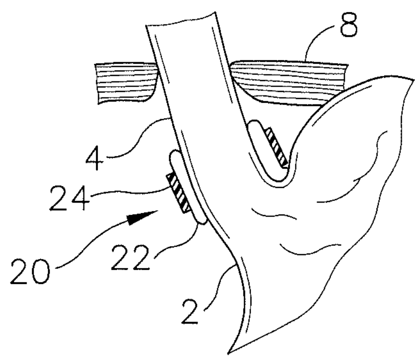
FIG. 3 depicts a cross-sectional view of the gastric band of FIG. 1, showing the band positioned around the gastro-esophageal junction of a patient in a deflated configuration.
Figure 4:
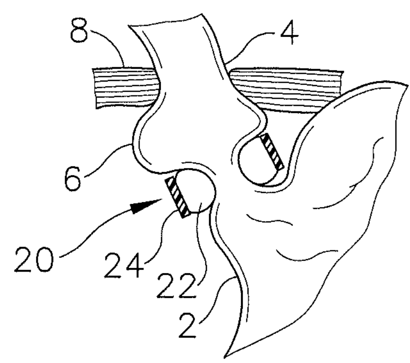
FIG. 4 depicts a cross-sectional view of the gastric band of FIG. 1, showing the band positioned around the gastro-esophageal junction of a patient in an inflated configuration to create a food intake restriction.

As shown in FIGS. 2-4, an installed gastric band (20) at least substantially encloses the upper portion of stomach (2) near the junction with esophagus (4) in the present example. FIG. 3 shows gastric band (20) in a deflated configuration, where bladder (22) contains little to no fluid, thereby maximizing the size of the stoma opening into stomach (2). FIG. 4 shows gastric band (20) in an inflated, fluid-filled configuration, where bladder (22) contains substantially more fluid than is shown in FIG. 3. In this configuration shown in FIG. 4, the pressure of gastric band (20) against stomach (2) is increased due to the fluid within bladder (22), thereby decreasing the stoma opening to create a food intake restriction. FIG. 4 also schematically illustrates the dilation of esophagus (4) above gastric band (20) to form an upper pouch (6) beneath the diaphragm muscle (8) of the patient.

II. Exemplary Pressure Sensing Device

It will be appreciated that it may be desirable to monitor and/or limit a drop or decrease in pressure within gastric band system (10). Alternatively, it may be desirable to monitor and/or limit spikes or increases of pressure within gastric band system (10), such as when fluid is being added to gastric band system (10) and/or in other settings. As a result, it may be desirable to provide a system that provides the user with knowledge of the pressure within gastric band system (10) or with a means for limiting the pressure changes within gastric band system (10). It will be appreciated that a needle with a syringe attached, which may be inserted into septum (16) to draw fluid out, may cause significant changes in pressure within gastric band (20) or more generally in gastric band system (10). Such a pressure drop or spike may occur upon inserting the needle into septum (16) or may occur during the removal or addition of fluid. As a result, when removing fluid from gastric band system (10), it may be desirable to monitor or limit the decrease in pressure associated with the removal of the fluid. Alternatively, it may also be desirable to monitor or limit the amount of pressure added to gastric band system (10) caused by adding fluid to gastric band system (10).

Figure 5:
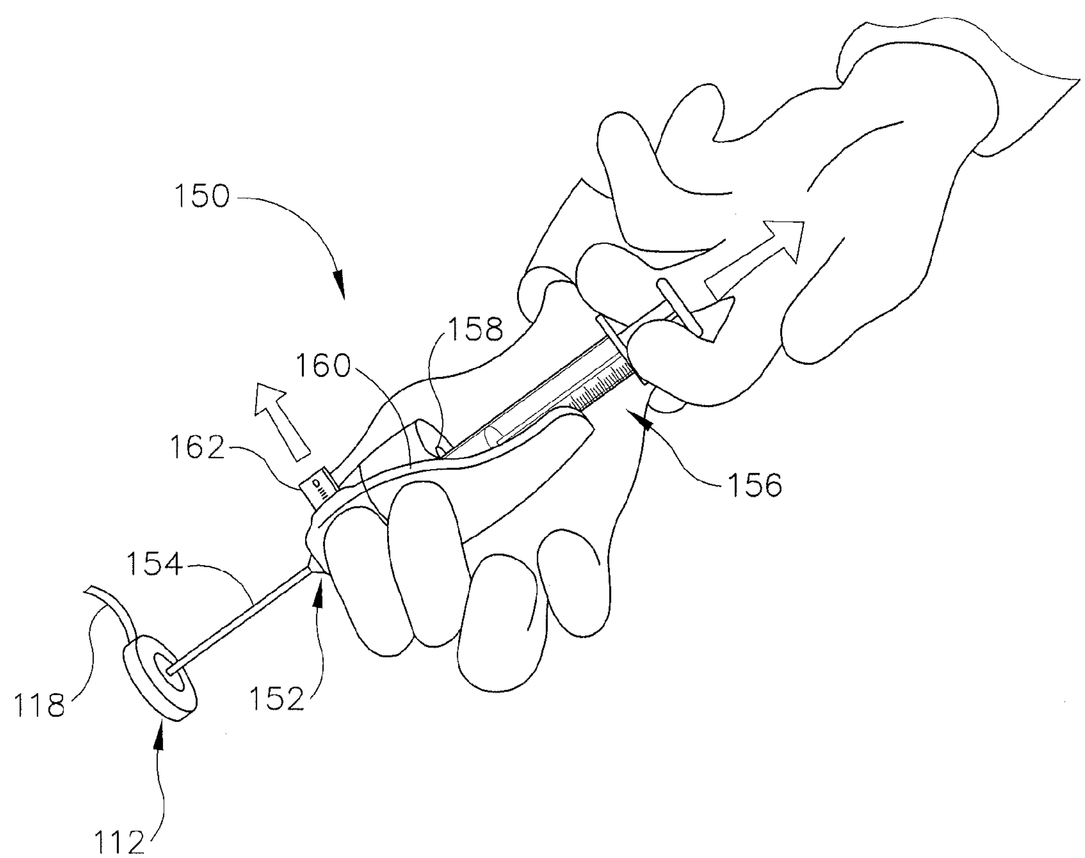
FIG. 5 depicts a perspective view of an exemplary pressure control system.
Figure 6:
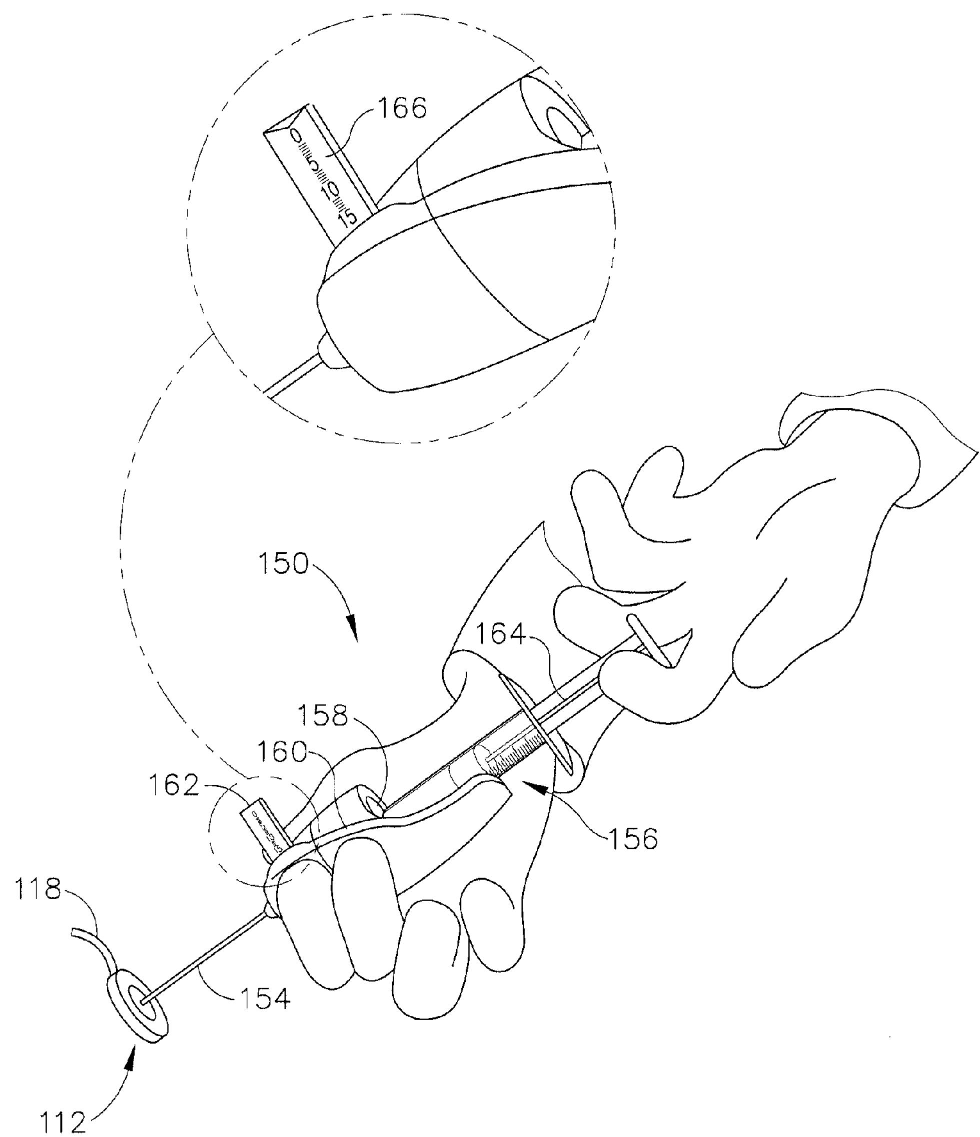
FIG. 6 depicts a perspective view of the pressure control system of FIG. 5, showing a plunger drawn from a syringe.

FIGS. 5-6 depict a version of a pressure control system (150). Pressure control system (150) may be used with an injection port (112), which is connected to catheter (118) as shown in the illustrated version. Pressure control system (150) is operable to work seamlessly with any closed fluid implantable biological system or device involving the addition or removal of fluid. Other uses will be apparent to one of ordinary skill in the art in view of the teachings herein.

Pressure control system (150) comprises a syringe (156), needle (154), and a pressure monitoring device (152). In the illustrated version, pressure monitoring device (152) is positioned between syringe (156) and needle (154). However, other arrangements may be used as well. For example, pressure monitoring device (152) may be connected only to syringe (156) without being in contact with needle (154). Any suitable arrangement may be used as would be apparent to one of ordinary skill in the art in view of the teachings herein.

Needle (154) comprises a standard gauge Huber needle configured to be inserted into injection port (112). Needle (154) further comprises an interface (178) to connect to a body (160) of pressure monitoring device (152). Interface (178) between needle (154) and the body (160) of pressure monitoring device (152) may comprise a screw fit, snap fit, luer lock, or any other suitable interface (178) as would be apparent to one of ordinary skill in the art in view of the teachings herein.

Syringe (156) comprises a syringe body modified to fit pressure monitoring device (152), The syringe body is shaped to receive a plunger (164) extending through the syringe body. A proximal portion of body (160) defines an opening (158) shaped to fit syringe (156). Syringe (156) may be filled with a fluid prior to inserting syringe (156) into opening (158) or may be filled after inserting syringe (156) into opening (158). Of course, syringe (156) need not necessarily be modified. For instance, body (160) may be configured to receive a conventional syringe barrel, and may include a screw fitting, snap fitting, luer lock, or any other suitable feature to interface with a conventional syringe barrel, In other words, some versions of pressure control system (150) may be viewed as an adapter for a conventional syringe and Huber needle. In some other versions, pressure control system (150) is formed as a unitary construction with syringe (156) and/or needle (154).

Body (160) of pressure monitoring device (152) is shaped to have a contoured surface such that a user may easily grasp pressure monitoring device (152) during use, However, any suitable shape for body (160) may be used as would be apparent to one of ordinary skill in the art in view of the teachings herein. Body (160) comprises a palm-side portion that may be positioned in the palm of a user during use and a gauge-side portion generally opposite to the palm-side portion. The gauge-side portion comprises a pressure gauge meter (162) in this example. Pressure gauge meter (162) comprises a sliding gauge extending transversely from body (160) and such that the sliding gauge faces the user. Thus, as body (160) rests in the user's hands during use, it will be appreciated that the user will have direct line of sight to pressure gauge meter (162). Furthermore, the user will simultaneously be able to view the position of injection port (112) as well while fluid is being drawn through injection port (112) with syringe (156). Pressure gauge meter (162) transversely extends and retracts based on the pressure within syringe (156). For example, as pressure drops, then pressure gauge meter (162) extends farther thereby revealing more of pressure gauge meter (162). Other configurations are possible with pressure gauge meter (162) as would be apparent to one of ordinary skill in the art in view of the teachings herein. For example, pressure gauge meter (162) may be configured to retract as pressure drops and extend as pressure increases.

As seen in FIG. 6, when the user draws plunger (164) of syringe (156), the decrease in pressure caused by drawing plunger (164) retracts pressure gauge meter (162) transversely. In other words, while conventional sliding pressure meters may extend transversely to an extent associated with fluid pressure increases, pressure gauge meter (162) of the present example may retract transversely to an extent associated with fluid pressure decreases. Of course, pressure gauge meter (162) may also extend transversely to an extent associated with fluid pressure increases. Pressure gauge meter (162) may comprise a series of graduated markings (166) to represent various pressure levels. Furthermore, in some versions, pressure gauge meter (162) may comprise several discrete markings to represent various pressure ranges, where the markings may comprise, for example varied color backgrounds. For example: a white colored background may be used to designate a range of pressure readings that present little or no risks to gastric band system (10); an orange colored background may be used to designate a different range of pressure readings that present moderate risks to gastric band system (10); and a red colored background may be used to designate a range of pressure readings that present substantial risks to gastric band system (10). Other various color schemes or other forms of visually representing various risk levels may be used as would be apparent to one of ordinary skill in the art in view of the teachings herein. In the above-described version, three colored sections are used, but other suitable numbers and/or configurations may be used as well.

As the user draws plunger (164) and removes fluid, the user can monitor pressure gauge meter (162) as it extends by watching graduated markings (166) to determine if the pressure is dropping too quickly or if the pressure is dropping at an acceptable rate. In the present example, the pressure of fluid at pressure gauge meter (162) is approximately equal to, or roughly representative of, the fluid pressure of gastric band system (10) since the entire system is a closed fluid circuit. Once an acceptable level is reached as determined by monitoring graduated markings (166), the user can stop drawing plunger (164). While the illustrated version depicts a transversely extending gauge, any suitable gauge may be used to convey to a user the decrease in pressure within syringe (156) including, but not limited to, a digital pressure gauge, an analog dial, etc. For instance, pressure gauge meter (162) may be configured in accordance with any teachings in U.S. Pub. No. 2008/0015406, entitled "External Mechanical Pressure Sensor for Gastric Band Pressure Measurements," published Jan. 17, 2008, and issued Apr. 19, 2011 as U.S. Pat. No. 7,927,270, the disclosure of which is incorporated by reference herein. In some versions (e.g., where pressure gauge meter (162) is digital, etc.), pressure gauge meter (162) may be programmed with certain pressure levels to provide an alert, lockdown of operation of syringe (156), and/or other results based on the type of gastric band system (10) or other type of system with which syringe (156) is to be used. Other suitable gauges will be apparent to one of ordinary skill in the art in view of the teachings herein.

Figure 7:
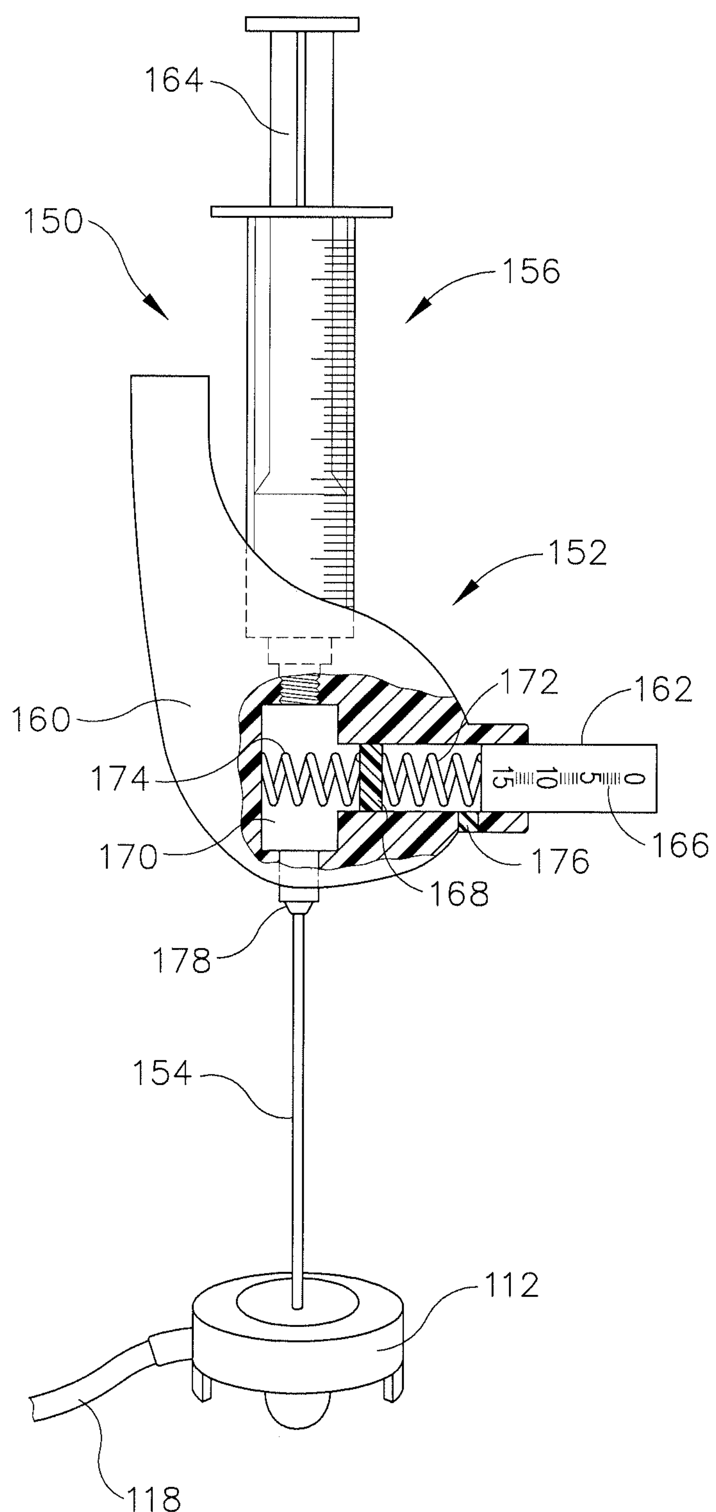
FIG. 7 depicts a side, partially cross-sectional view of the pressure control system of FIG. 5, showing a plunger drawn from a syringe.

FIG. 7 depicts a partial cross sectional view of pressure monitoring device (152).

Pressure monitoring device (152) further comprises a piston (168) within a hollow T-shaped chamber (170). Piston (168) is in communication with pressure gauge meter (162) such that piston (168) and pressure gauge meter (162) slide unitarily with each other relative to body (160). In the illustrated version, piston (168) is coaxially positioned in relation to pressure gauge meter (162); however, other suitable configurations will be apparent to one of ordinary skill in the art in view of the teachings herein.

A first coil spring (172) is positioned on one side of piston (168) and bears against both piston (168) and body (160). In some versions, first coil spring (172) is wrapped coaxially about a shaft (not shown) that couples pressure gauge meter (162) with body (160). A second coil spring (174) is positioned on the opposite side of piston (168). Second spring (174) also bears against both piston (168) and body (160). Coil springs (172, 174) have substantially the same spring constant and thus coil springs (172, 174) together bias piston (168) to a selected position while also allowing piston (168) to move in either direction from that selected position. As seen in the illustrated version, T-shaped chamber (170) is in fluid communication with syringe (156) and needle (154) by being positioned between syringe (156) and needle (154). Accordingly, if there is neither a pressure drop nor an increase in pressure, piston (168) remains substantially stationary within T-shaped chamber (170), thereby causing pressure gauge meter (162) to provide a zero, or neutral pressure reading. Furthermore, first spring (172) and second spring (174) are pressure calibrated such that pressure changes within T-shaped chamber (170) acting upon piston (168) translate to repeatable changes in the effective length of first spring (172) and second spring (174). Thus, if the pressure drops, perhaps through drawing plunger (164) of syringe (156), then piston (168) will accordingly be affected by the pressure drop, causing piston (168) and pressure gauge meter (162) to unitarily move toward second spring (174). Pressure gauge meter (162) will thus provide a pressure reading corresponding to the decreased pressure acting upon piston (168). Alternatively, if pressure increases within T-shaped chamber (170), such as by advancing plunger (164), piston (168) moves away from second spring (174), thereby pushing pressure gauge meter (162) transversely away from body (160) to provide a reading corresponding to the increased pressure in T-shaped chamber (170).

In some versions, pressure monitoring device (152) may further comprise a relief valve (176) where relief valve (176) is able to relieve pressure within T-shaped chamber (170) such that back pressure does not affect the pressure reading output provided by pressure gauge meter (162). Relief valve (176) may comprise a spring valve, such as those available by Value Plastics or Hackey Roberts, but any suitable spring valve may be used as would be apparent to one of ordinary skill in the art in view of the teachings herein. Additionally, relief valve (176) need not be limited to a spring valve, but any suitable valve may be used in view of the teachings herein. Alternatively, relief valve (176) may simply be omitted.

Furthermore, pressure monitoring device (152) may also comprise a safety valve (not shown) in communication with, for example, needle (154) such that at a particular pressure, the safety valve opens, which causes external air, rather than more fluid, to be drawn into T-shaped chamber (170) and syringe (156). As a result, if fluid is being drawn by syringe (156), the total reduction in pressure caused by drawing fluid with syringe (156) may be limited by the safety valve. Accordingly, the safety valve may be pressure calibrated such that the safety valve only triggers once a predetermined pressure drop is reached. In particular, threshold pressures to the safety valve may be set to, for example, −30 mmHg (for pressure drops) or 300 mmHg (for pressure rises). However, any suitable pressure threshold may be used as would be apparent to one of ordinary skill in the art in view of the teachings herein. It should also be understood that a safety valve may be calibrated to provide a relief when the rate of change in pressure exceeds a threshold rate (e.g., in addition to or in lieu of being calibrated to provide relief when the actual value of pressure exceeds a threshold value).

Figure 8:
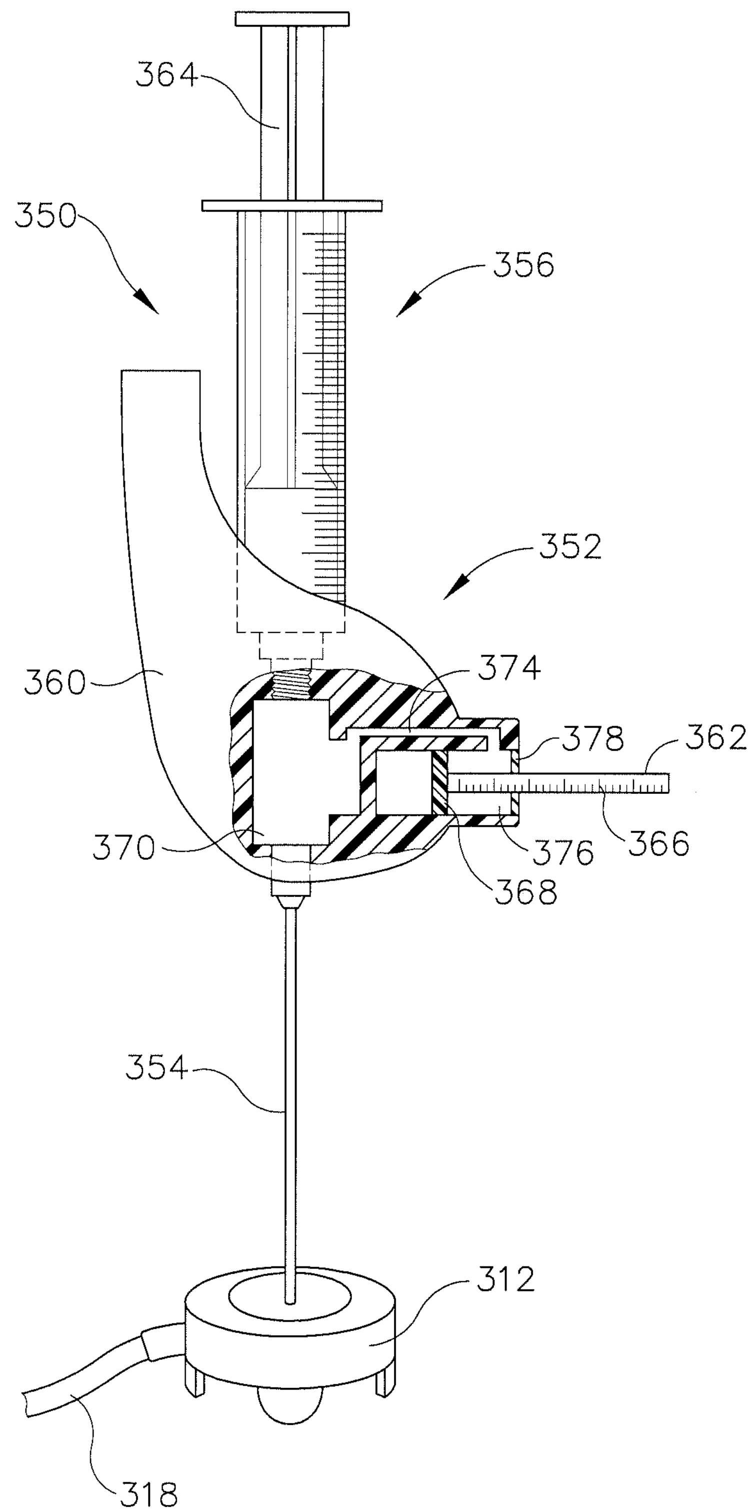
FIG. 8 depicts a side, partially cross-sectional view of an alternative version of a pressure control system, showing a plunger drawn from a syringe.

FIG. 8 shows an alternative version of a pressure control system (350) comprising a pressure monitoring device (352) having a body (360) connecting a syringe (356) and a needle (354). Needle (354) may be used with an injection port (312) in communication with a catheter (318). Syringe (356) comprises a plunger (364) extending through syringe (356). The aforementioned components regarding FIG. 8 are substantially similar to corresponding components discussed with respect to FIG. 7. However, variations may be used as would be apparent to one of ordinary skill in the art in view of the teachings herein.

A T-shaped chamber (370) is formed within body (360), which provides communication between syringe (356) and needle (354). T-shaped chamber (370) is further in fluid communication with a fluid channel (374), which leads to a piston chamber (376). A piston (368) is positioned within piston chamber (376), and piston (368) is coupled to a pressure gauge meter (362) such that movement of piston (368) causes corresponding movement of pressure gauge meter (362). A dynamic seal (378) is positioned around pressure gauge meter (362) so as to provide a fluid tight seal while allowing pressure gauge meter (362) to translate relative to body (360). Because the space between piston (368) and dynamic seal (378) is in fluid communication with T-shaped chamber (370) via fluid channel (374), a drop in pressure in T-shaped chamber (370) will also cause a drop in pressure in piston chamber (376). As pressure drops in piston chamber (376), piston (368) moves towards dynamic seal (378) to compensate for the drop in pressure, thereby causing pressure gauge meter (362) to translate away from body (360). In cases where pressure increases within piston chamber (376), piston (368) moves away from dynamic seal (378), and pressure gauge meter (362) will accordingly be retracted into body (360). Piston chamber (376) in conjunction with piston (368) and dynamic seal (378) is calibrated such that pressure drops result in repeatable translation by pressure gauge meter (362). A user may use graduated markings (366) on pressure gauge meter (362) to monitor the pressure drop or increase.

III. Exemplary Removable Pressure Sensing Device

It will be appreciated that in some situations, it may be desirable to use a device adaptable to a standard syringe such that the device may be used to provide knowledge of a pressure change cause by drawing a plunger of a syringe. Additionally, it may be desirable to have a device able to simply prevent the further drawing of a plunger once the pressure change exceeds a certain threshold.

Figure 9:
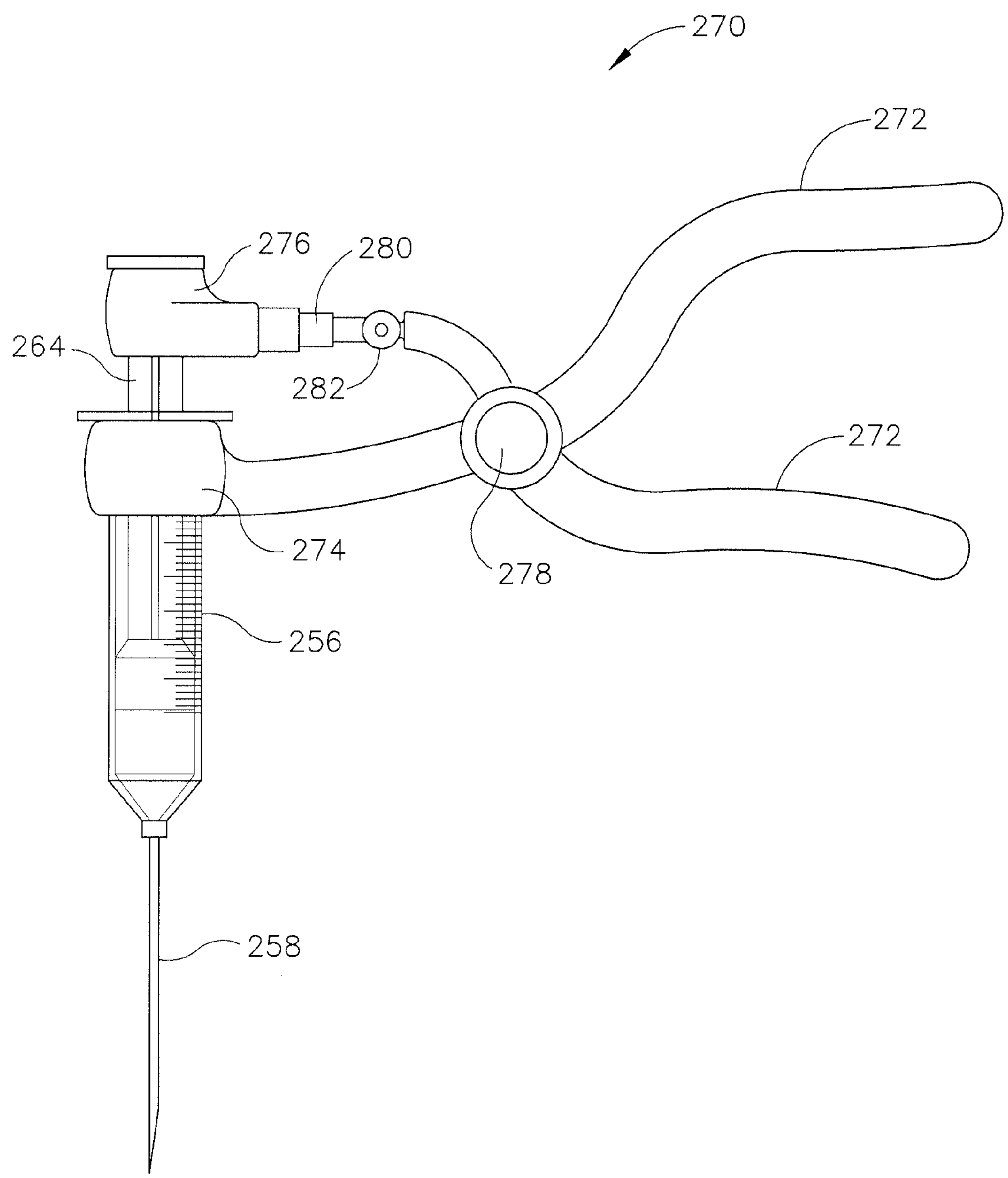
FIG. 9 depicts a side view of a pressure governor being used with a syringe.

FIG. 9 depicts a pressure governor (270) for use with a conventional syringe (256). Pressure governor (270) comprises a pair of pivoting handles (272), a syringe barrel holder (274), a force limiter (278), and a plunger holder (276). Pressure governor (270), and more particularly, syringe holder (274), are used to secure a syringe (256). Plunger holder (276) is then secured to plunger (264) of syringe (256). Plunger holder (276) is in communication with a telescopic arm (280), which is in communication with a hinge (282). As a result, telescopic arm (280) and hinge (282) in conjunction with plunger holder (276) enable plunger (264) to be drawn linearly in relation to syringe (256) by plunger holder (276) as handles (272) are squeezed toward each other. In the illustrated version, handles (272) comprise two contoured handles connected to force limiter (278). Handles (272) are attached so as to pivot about force limiter (278). Syringe holder (274) is pivotally attached to force limiter (278), and plunger holder (276) is in communication with force limiter (278) through telescopic arm (280) and hinge (282).

Syringe holder (274) may secure syringe (256) by using, for example, a tensioned loop having an opening that syringe (256) may be pressed into to snap syringe (256) into syringe holder (274). Plunger holder (276) may comprise generally a loop that is sized such that as plunger holder (276) is pulled away from syringe holder (274), plunger holder (276) pulls plunger (264) to draw fluid into syringe (256). Other various shapes for syringe holder (274) and plunger holder (276) will be apparent to one of ordinary skill in the art in view of the teachings herein. As handles (272) are squeezed together, syringe holder (274) and plunger holder (276) separate in a generally linear manner, which draws plunger (264) from syringe (256), thereby drawing fluid through a needle (258) into syringe (256).

Force limiter (278) is calibrated such that if a user exceeds a certain predetermined level of rotational force by squeezing handles (272) together, force limiter (278) prevents handles (272) from being squeezed together further, such that force limiter (278) acts as a governor. As a result, plunger (264) can only be drawn from syringe (256) with a correspondingly limited amount of force. Once the predetermined force is exceeded, plunger (264) can no longer be drawn from syringe (256) until the force of squeezing handles (272) is reduced. Additionally, it will be appreciated that the level of force regulated by force limiter (278) may correspond and/or correlate generally to a level or rate of pressure drop caused by syringe (256) with plunger (264) being drawn. As a result, it will be appreciated that the level of pressure drop within a gastric band system (such as one depicted in FIGS. 1-4) in communication with syringe (256) caused by drawing fluid into syringe (256) can be limited with force limiter (278). Various suitable ways in which force limiter (278) may be configured will be apparent to those of ordinary skill in the art in view of the teachings herein.

Figure 10:
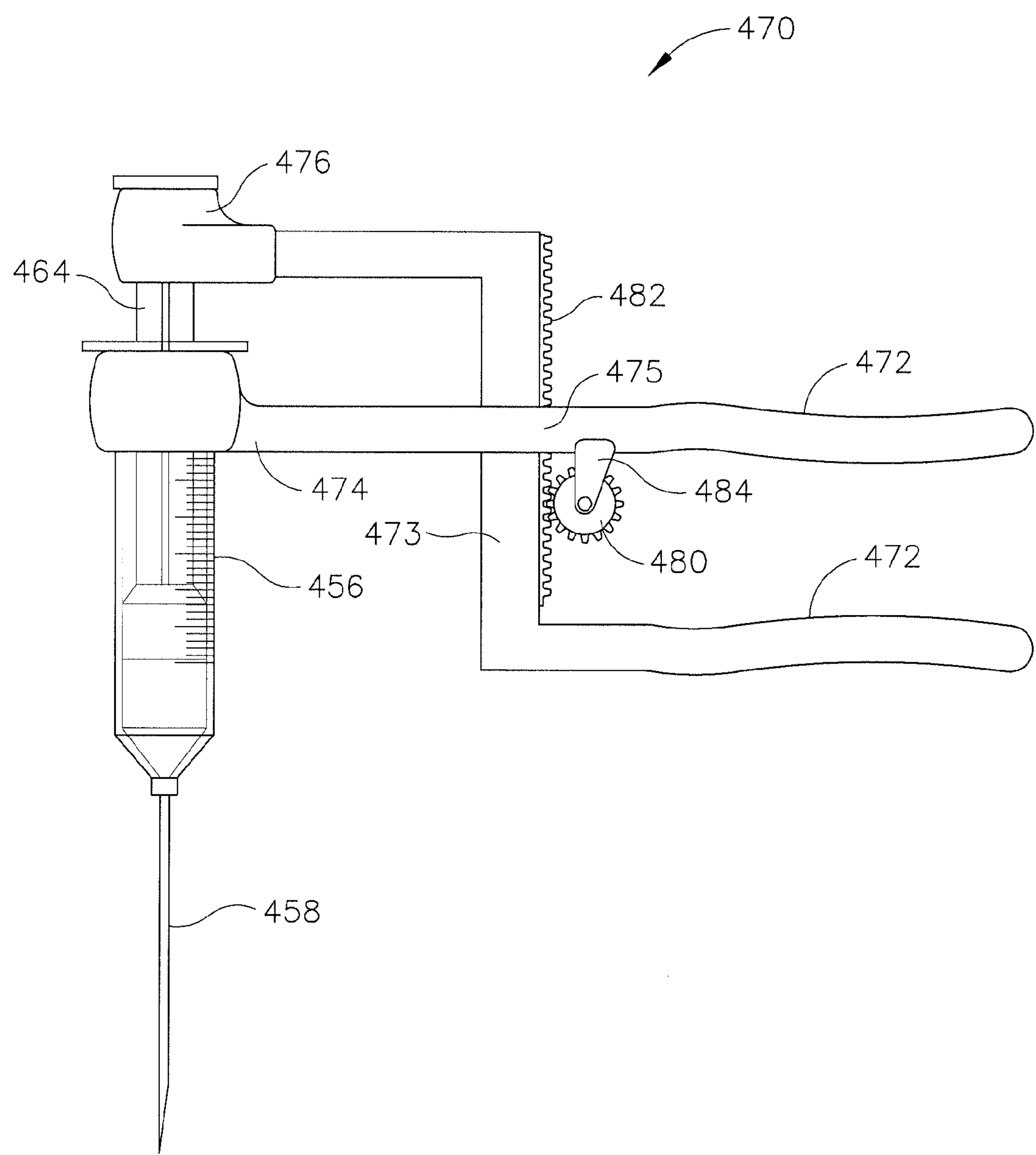
FIG. 10 depicts a side view of an alternative version of a pressure governor being used with a syringe.

FIG. 10 shows an alternative version of a pressure governor (470) comprising a pair of handles (472) in communication with a plunger holder (476) and a syringe holder (474). In particular, one handle (472) is coupled with syringe holder (474) by a horizontal portion (475) while the other handle (472) is coupled with plunger holder (476) by a vertical portion (473). Vertical portion (473) is slidably disposed relative to horizontal portion (475), such that vertical portion (473) moves linearly upward relative to horizontal portion (475) when handles (472) are squeezed together. Vertical portion (473) includes a rack (482), which is meshingly engaged with a pinion (480), which is secured to horizontal portion (475). Rack (482) and pinion (480) operate where rack (482) moves linearly in relation to pinion (480) to enable handles (472) to be squeezed linearly together. When handles (472) are squeezed together, rack (482) rotates pinion (480), and plunger holder (476) and syringe holder (474) separate from each other, thereby drawing plunger (464) from syringe (456), which results in drawing fluid through a needle (458). Plunger holder (476) and syringe holder (474) are positioned roughly parallel to each other such that as handles (472) are being squeezed together, plunger holder (476) and syringe holder (474) separate in a linear manner to facilitate smooth drawing of plunger (464).

Pinion (480) is further in communication with a governor (484), which prevents the torque applied to pinion (480) from exceeding a predetermined amount. It will be appreciated that a predetermined amount of torque applied to pinion (480) may correspond and/or correlate to a level or rate of pressure drop within syringe (456). As a result, it will also be appreciated that the degree of pressure drop caused by syringe (456) acting on a gastric band system may be limited by governor (484) in conjunction with rack (482) and pinion (480). Governor (484) may be calibrated to any appropriate torque or force as would be apparent to one of ordinary skill in the art in view of the teachings herein. Various suitable ways in which governor (484) may be configured will also be apparent to those of ordinary skill in the art in view of the teachings herein.

It will become readily apparent to those skilled in the art that examples described herein may have applicability to other types of implantable bands. For example, bands are used for the treatment of fecal incontinence. One such band is described in U.S. Pat. No. 6,461,292, entitled "Anal Incontinence Treatment with Wireless Energy Supply," issued Oct. 8, 2002, the disclosure of which is incorporated by reference herein. Bands can also be used to treat urinary incontinence. One such band is described in U.S. Pat. No. 7,621,863, entitled "Urinary Incontinence Treatment with Wireless Energy Supply," issued Nov. 24, 2009, the disclosure of which is incorporated by reference herein. Bands can also be used to treat heartburn and/or acid reflux. One such band is described in U.S. Pat. No. 6,470,892, entitled "Mechanical Heartburn and Reflux Treatment," issued Oct. 29, 2002, the disclosure of which is incorporated by reference herein. Bands can also be used to treat impotence. One such band is described in U.S. Pat. No. 7,442,165, entitled "Penile Prosthesis," issued Oct. 28, 2008, the disclosure of which is incorporated by reference herein. Various ways in which the teachings herein may be incorporated with the teachings of these patent references will be apparent to those of ordinary skill in the art.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Versions of the present invention have application in conventional endoscopic and open surgical instrumentation as well as application in robotic-assisted surgery.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:

(a) a pressure monitoring device, wherein the pressure monitoring device is configured to be in communication with a syringe, wherein the pressure monitoring device is configured to have a predetermined threshold pressure;

(b) an actuation portion, wherein the actuation portion comprises a first elongate member and a second elongate member coupled at a pivot joint, wherein the first elongate member comprises a plunger holder secured to a plunger of the syringe, wherein the second elongate member comprises a syringe holder secured to a barrel of the syringe, and wherein the actuation portion is operable to draw the plunger of the syringe from the barrel of the syringe;

(c) a visual indicator, wherein the visual indicator is in communication with the pressure monitoring device, wherein the visual indicator is associated with the predetermined threshold pressure; and (d) a stopping mechanism in communication with the actuation portion, wherein the stopping mechanism forms the pivot joint of the actuation portion, and wherein the stopping mechanism is configured to prevent further actuation of the actuation portion in response to a sensed pressure exceeding or falling below the predetermined threshold pressure.

2. The apparatus of claim 1, further comprising a release mechanism, wherein the release mechanism is configured to prevent the syringe from drawing fluid.

3. The apparatus of claim 2, wherein the release mechanism comprises a release valve.

4. The apparatus of claim 1, wherein the predetermined threshold pressure is a pressure drop value.

5. The apparatus of claim 4, wherein the predetermined threshold pressure is between approximately −30 mmHg and −60 mmHg.

6. The apparatus of claim 1, further comprising an implantable band system in fluid communication with the pressure monitoring device.

* * * * *